United States Patent [19]

Kienholz et al.

[11] 4,267,974

[45] May 19, 1981

[54] NEBULIZER DEVICE

[75] Inventors: Charles M. Kienholz, Upland; Clifford D. Bennett, Alta Loma, both of Calif.

[73] Assignee: C. R. Bard, Inc., Murray Hill, N.J.

[21] Appl. No.: 60,393

[22] Filed: Jul. 25, 1979

[51] Int. Cl.³ .................... B67D 5/38; A61M 11/06
[52] U.S. Cl. ................... 239/74; 128/200.18; 128/200.21; 128/203.25; 128/203.27; 239/121; 239/309; 239/338; 261/78 A; 261/142; 261/DIG. 65
[58] Field of Search ............... 239/73, 74, 135, 338, 239/347, 348, 370, 416, 428, 430–434, 121, 122, 272, 124, 309; 261/78 A, 142, DIG. 65; 55/238, 257 C; 128/200.18, 200.21, 203.27, 203.26, 203.25

[56] References Cited

U.S. PATENT DOCUMENTS

| 1,832,916 | 11/1931 | Purdie | 128/200.21 |
|---|---|---|---|
| 3,208,639 | 9/1965 | Marwell et al. | 261/DIG. 65 |
| 3,652,015 | 3/1972 | Beall | 239/338 |
| 3,915,386 | 10/1975 | Vora | 239/338 |
| 4,011,288 | 3/1977 | Assenheimer et al. | 261/DIG. 65 |
| 4,098,573 | 7/1978 | Gunther | 261/142 |
| 4,150,071 | 4/1979 | Pecina | 239/370 |
| 4,177,945 | 12/1979 | Schwartz et al. | 239/338 |

Primary Examiner—Bruce H. Stoner, Jr.
Assistant Examiner—Michael J. Forman
Attorney, Agent, or Firm—Richard H. Zaitlen

[57] ABSTRACT

A nebulizer device for producing an aerosol spray via a flow of gas at varying oxygen concentrations is disclosed. The nebulizer device comprises a body defining an initial nebulization chamber, a subsequent baffling chamber and a venturi formed therebetween. Air intake ports are disposed on the body adjacent the nebulization chamber for providing the nebulization chamber with air in predetermined quantities. Regulating means are disposed about the nebulization chamber for regulating the flow of the air through the intake ports. An aerosol system for producing an aerosol of fine particles of liquid is located in the nebulization chamber upstream of the venturi such that the flow of the aerosol spray through the venturi encourages the atmospheric fluid to enter the device through the intake ports thereby diluting the aerosol. The venturi is located downstream of the intake ports and increases the flow rate of the atmospheric fluid through the intake ports. The baffling chamber is provided with an outlet for directing the aerosol out of the baffling chamber.

22 Claims, 7 Drawing Figures

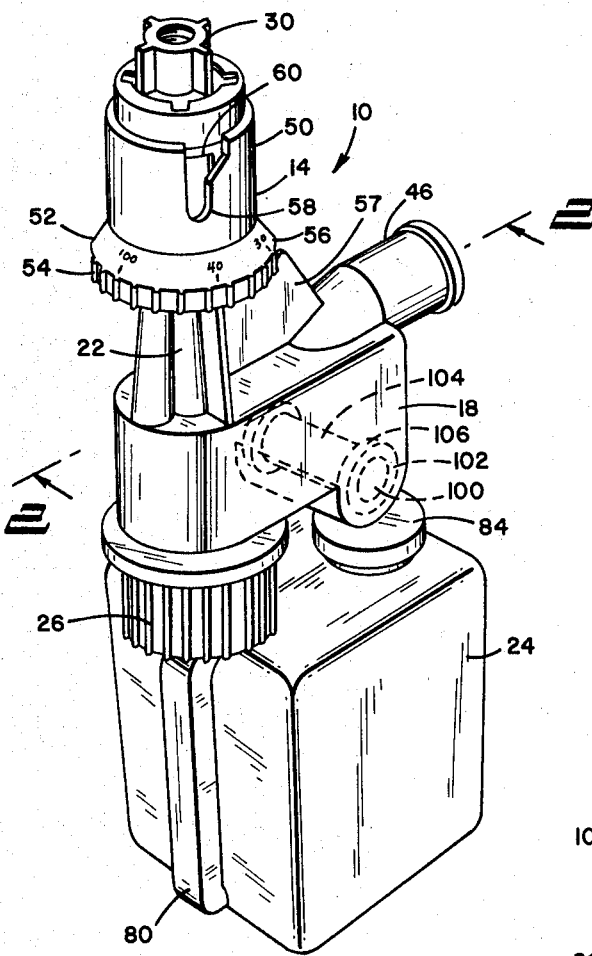
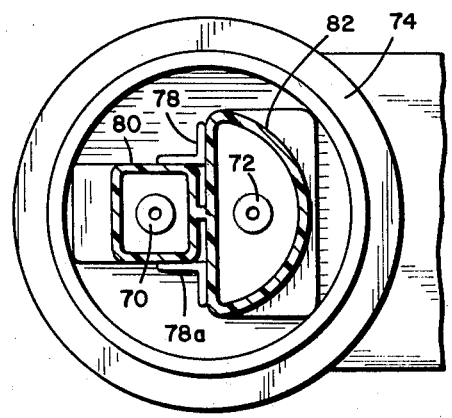
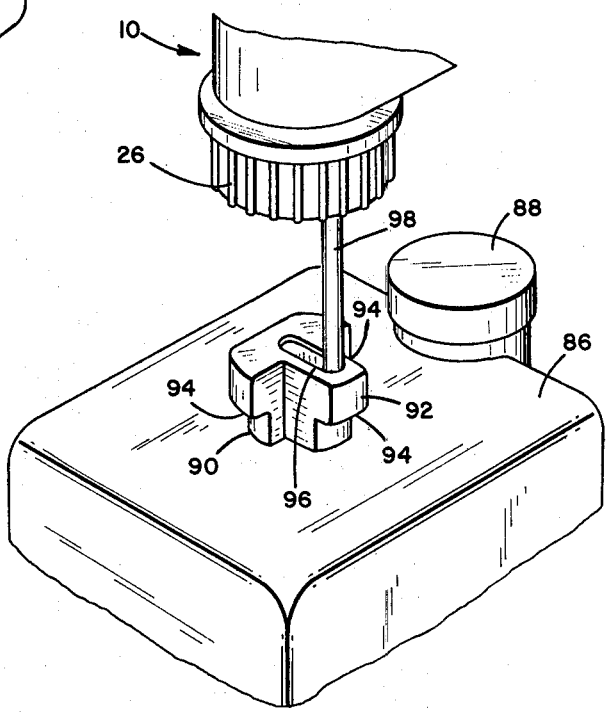

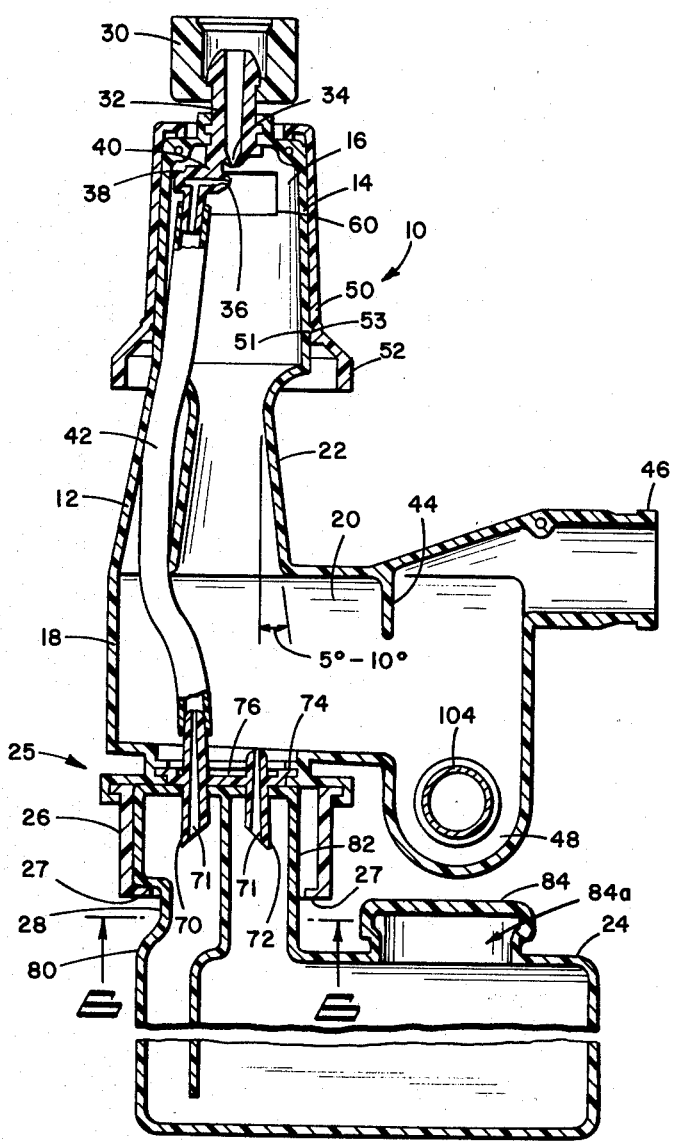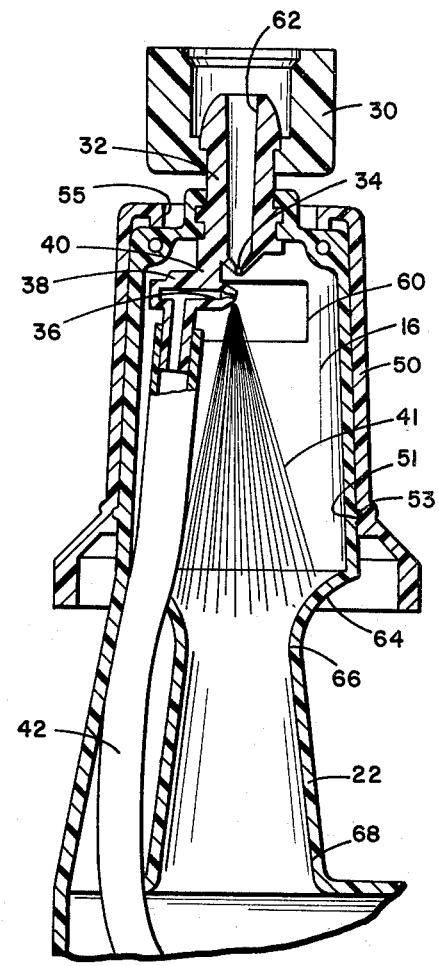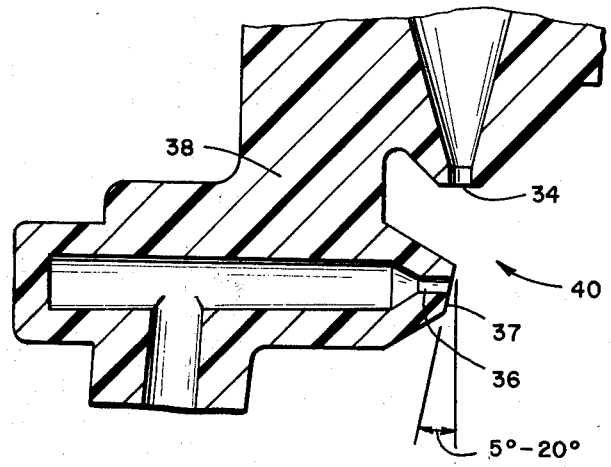

NEBULIZER DEVICE

BACKGROUND OF THE INVENTION

1. Field of the Invention

This invention relates to inhalation therapy devices, and more particularly, to the design and construction of a nebulizer device for producing an aerosol spray delivered via flow of gas at varying oxygen concentrations.

2. Prior Art

It has been determined that a number of respiratory ailments can be treated by the inhalation of an aerosol spray of finely divided particles of water or other liquid medicaments. Devices referred to generally as nebulizer devices have evolved which are designed to produce such an aerosol spray. Nebulizers introduce a stream of pressurized gas, usually oxygen, into a chamber which entrains liquid particles so as to form the spray. Examples of these devices are shown in U.S. Pat. Nos. 3,652,015; 3,836,079; 3,915,386; and 4,036,919. The nebulizers shown in these patents are designed to operate with oxygen as the gas used to form the aerosol spray. This is because pressurized oxygen is usually available in each hospital room or at least in certain rooms. Care had to be exercised both in the design of the nebulizer and its operation as different patient conditions require different amounts of oxygen. The nebulizer devices of the prior art have been designed such that the lowest oxygen concentrations delivered to the patient were approximately 35% oxygen.

However, under certain conditions, it is believed beneficial if the oxygen is diluted with air such that the volume percent of oxygen being delivered to the patient approaches as much as possible the amount of oxygen in air—approximately 21%. To achieve lower oxygen concentrations, expensive regulators or blending equipment had to be used in combination with the nebulizer so as to reduce the oxygen concentration delivered to the patient to below 35%.

Another problem associated with some prior art nebulizers was in the fastening systems used to join the nebulizer to an associated bottle containing the liquid. This is especially important when the bottle is prefilled with a sterilized liquid. In the past, some fastening systems used an externally formed return tube provided on the nebulizer such that liquid which was not entrained by the gas and carried out of the nebulizer could be returned to the associated bottle. This not only required special construction of the nebulizer, but of the bottle as well. Further, such construction prevents a sterile field from being maintained, as during attachment of the nebulizer to the bottle, a separate puncture site had to be made in the bottle. Other nebulizers used a bottle having a very wide mouth such that liquid could be removed from and returned to the bottle through the mouth. Again, sterility of the liquid in such a case is difficult to maintain.

Finally, the prior art nebulizer devices generally required an aerosol-producing system which included an impaction post used to break up the liquid into fine droplets. The post had to be specifically located in order to insure that fine droplets were formed.

The present invention provides answers to these as well as other problems associated with prior art devices. In addition, the present invention provides such answers in a relatively straightforward manner enabling the device of the present invention to be easily manufactured and at a relatively low cost.

SUMMARY OF THE INVENTION

Broadly, the present invention is directed to a nebulizer device for producing an aerosol spray, delivered via a flow of gas at varying concentrations of oxygen. The device solves a number of problems associated with the prior art by means of a number of unique and novel features. The nebulizer device of the present invention is designed for use in gas-flow circuitry wherein pressurized oxygen is the driving gas. However, the device of the present invention permits the addition of ambient air such that the amount of oxygen concentration reaching the patient can be regulated from approximately 100% down to approximately 28%. The nebulizer device comprises a body defining an initial nebulization chamber, a subsequent baffling chamber and a venturi formed therebetween. A coupling is provided on the body for connecting the nebulization chamber to a source of pressurized oxygen. Intake ports are disposed in the body adjacent the nebulization chamber and enable atmospheric air to flow into the nebulization chamber. A rotatable member is circumferentially disposed about the body adjacent the nebulization chamber. The rotatable member has uniquely shaped openings for regulating the amount and encouraging the flow of atmospheric fluid through the intake ports. An aerosol means for producing an aerosal spray of finely divided liquid particles is located in the nebulization chamber upstream of the venturi such that the pressurized oxygen gas used to form the aerosal spray can be diluted by the intake of atmospheric air. The body is configured so as to provide a straight path for the spray from the nebulization chamber to the baffling chamber.

The venturi is specifically located downstream of the intake ports and is defined by a converging section in flow communication with the nebulization chamber, and a diverging section in flow communication with the baffling chamber. The venturi is configured for increasing the flow rate of the air into the device. This increases the amount of air entrained in the aerosol spray and this decreases the oxygen concentration. Finally, the baffling chamber is equipped with an outlet port such that the aerosol spray can be directed out of the baffling chamber and to the ultimate end use.

It is believed that the ability of the nebulizer device of the present invention to achieve dilution of the oxygen such that the outflow can be as low as approximately 28% oxygen is achieved by a combination of the venturi, the intake ports, and the shape of the openings on the rotatable member. It is to be understood, however, that modifications of these three elements are also within the scope of this invention. For example, it has been determined that even without the unique shape of the openings on the rotatable member, oxygen content of the stream flowing out of the device as low as approximately 30% can still be achieved.

Another aspect of the present invention which is an advantage over the prior art devices is the means used for joining the nebulizer device to an associated prefilled bottle. As stated above, in the past various joining systems were used which were complex and/or presented sterility problems. In the device of the present invention, first and second puncture probes are provided as part of a joining system which are formed on the bottom of the nebulizer device. These puncture probes are inserted into an associated bottle in a specific location. On of these probes provides a flow path for liquid to the aerosol means, while the other probe permits liquid which has collected in the nebulizer device to return back to the bottle. The present joining system thus enables prefilled bottles to be easily joined to the nebulizer device without the need for any additional equipment or hook-up members. By the use of the joining system of the present invention, it is also believed that a substantially more sterile field can be achieved, as no additional hook-ups or wide mouth bottles need be used.

Yet another advantage of the present invention over the prior art is in connection with the means used to produce the aerosol spray. In the devices of the prior art, an impaction post was provided such that as the aerosol spray was created, it impacted upon the post. This caused the liquid entrained in the gas to be broken up into finely divided particles. In the device of the present invention, while such impaction post could be used, by providing a specifically shaped nozzle for delivering the liquid, an aerosol spray is created which is already comprised of finely divided liquid droplets. Thus, the need for such an impaction post is obviated.

In operating the device of the present invention, a prefilled bottle containing a liquid, usually purified water, is joined to the nebulizer device. More specifically, the two puncture probes are forced through the neck of the bottle such that both probes are in flow communication with the bottle. One of the probes is uded to direct the water from the bottle to the aerosol means, while the other probe is used to direct water collecting in the device back to the bottle. A locking ring on the nebulizer is secured to the bottle neck to insure that a tight seal is maintained therebetween. A source of pressurized gas is then joined to the device and is directed into the nebulization chamber. Here the nebulizing operation takes place, i.e., the gas is directed past a nozzle in flow communication with the water in the bottle. A venturi effect is created causing the water to be siphoned out of the bottle and sprayed into the nebulization chamber. The water is then entrained by the gas forming an aerosol spray which is directed through the remainder of the device. Because the nozzle which introduces the water into the nebulization chamber has a unique configuration, a shearing action is created whereby finely divided particles are produced.

It has been determined that many respiratory ailments can be treated by the use of finely divided liquid particles. Fine particles are desired because they can more readily flow into the respiratory tract. Thus, it is desirable to remove larger liquid particles from the spray being delivered to the patient. To help remove larger particles in the present invention, the aerosol spray flows through the venturi into the baffling chamber such that the larger particles impact on the baffling chamber walls. The baffling chamber is thus configured and located to help remove larger particles from the aerosol spray and also to collect such larger particles. Collected liquid is directed back into the bottle through the second probe.

In order to regulate the amount of oxygen being delivered to the patient, the body has a plurality of intake ports formed adjacent the nebulization chamber. These ports act in combination with the venturi and with a rotatable sleeve member to permit air to be drawn into the device. More specifically, as the sleeve member is rotated, shaped openings formed thereon are brought into alignment with the intake ports. Gas flowing through the venturi causes the air to be drawn into the device through the shaped openings and intake ports. As stated above, oxygen content as low as approximately 28% can be achieved by the device of the present invention. Rotating the sleeve in a specific direction closes off the ports and thus the aerosol delivered to the patient would contain approximately 100% oxygen. In this manner, the oxygen content of the aerosol delivered can be controlled within the range of approximately 28% to 100%.

The novel features which are believed to be characteristic of the invention, both as to its organization and method of operation, together with further objectives and advantages thereof will be better understood from the following description considered in connection with the accompanying drawings in which a presently preferred invention is illustrated by way of example. It is to be expressly understood, however, that the drawings are for the purpose of illustration and description only, and not intended as a definition of the limits of the invention.

BRIEF DESCRIPTION OF THE DRAWINGS

FIG. 1 is a perspective view of the nebulizer device of the present invention;

FIG. 2 is a cross-sectional view taken along lines 2—2 of FIG. 1 and showing the internal aspects of the nebulizer device of the present invention;

FIG. 3 is an enlarged cross-sectional view of the upper portion of the nebulizer device of the present invention;

FIG. 4 is an enlarged cross-sectional view of the nozzles used to form the aerosol spray in the present invention;

FIG. 5 is a perspective view showing the puncture probes of the present invention;

FIG. 6 is a bottom cross-sectional view showing the relationship of a associated bottle neck to the puncture probes shown in FIG. 5; and FIG. 7 is a perspective view showing a second embodiment for an associated bottle used in connection with the nebulizer device of the present invention.

DETAILED DESCRIPTION OF THE INVENTION

Referring first to FIGS. 1 and 2, one can see the nebulizer device 10 of the present invention. The nebulizer device 10 comprises a plastic body 12 having a tubular top section 14 defining a nebulization chamber 16, a generally rectangular bottom section 18 defining a baffling chamber 20 and a tubular venturi section 22 formed therebetween. The nebulizer device 10 is shown as being joined to an associated, generally rectangular plastic bottle 24. Bottle 24 preferably contains a purified liquid, such as water, which may be medicated and which is to be ultimately delivered to the patient in the form of an aerosol spray as hereinbelow described. In the preferred embodiment, bottle 24 is joined to the nebulizer device 10 by a uniquely configured joining assembly. This assembly includes a locking collar 26 which, when rotated, causes three equally spaced gripping members 27 to engage the neck region 28 of bottle 24. Locking collar 26 and gripping members 27 are configured to form a secure and clean connection between device 10 and bottle 24.

Adjacent the top of the nebulizer device 10 is a rotatable coupling 30 circumferentially disposed about a gas conduit 32. Coupling 30 is configured to be readily joined to a source of pressurized oxygen. Such couplings are well-known in the art and will not be described in detail herein. Usually, 100% oxygen is utilized and is supplied at a pressure of 50 PSI. Gas conduit 32 forms a first nozzle 34 for directing gas into the nebulization chamber 16. A second nozzle 36, generally perpendicular to nozzle 34, is formed on section 38. Section 38 is integrally joined to the conduit 32 by a downwardly extending section 40. Nozzles 34 and 36 form a means for producing a fine aerosol spray in the nebulization chamber 16 as described in detail hereinbelow.

Referring now to FIGS. 3 and 4, one can see the aerosol means, i.e. nozzles 34 and 36 in greater detail. Nozzles 34 and 36 are configured such that as pressurized gas flows through nozzle 34, it is directed across nozzle 36. This creates a venturi effect at the discharge end 37 of nozzle 36. Liquid is thus caused to be drawn up through conduit 42 and out through nozzle 36. Upon exiting, the liquid comes in contact with the gas jet spray created by nozzle 34. This action is enhanced by positioning nozzle 36 at an approximate right angle with respect to the axis of nozzle 34.

In the past, it was necessary to provide an impaction post directly beneath nozzle 36 such that one could be assured that the liquid would be broken up into fine particles. In the device 10 of the present invention, the need for such impaction post is obviated. This is achieved by forming discharge end 37 of nozzle 36 at an angle of approximately 5° to 20° and preferably 10° to 15°, away from the axis of the nozzle 34, and by providing a straight path for the spray all the way into the baffling chamber 20. It is believed that by angling face 37, as the liquid exits from nozzle 36, a shearing action takes place which causes the liquid to break up into fine particles and to form a generally conical aerosol spray. This spray is generally indicated by numeral 41. As spray 41 proceeds through the nebulization chamber 16, many of the larger particles are caused to impact on venturi 22 which acts as an initial baffle, as well as on the bottom of baffling chamber 20. Larger particles which impact on venturi 22 flow into chamber 20 where they collect. The remainder of the spray 41 flows through venturi 22 into the baffling chamber 20. The spray 41 is then directed out of chamber 20 by means of tubular conduit 46. To help insure that large particles are not delivered to the patient, another baffle plate 44 is also located in chamber 20.

Liquid which does not flow out of the device 10 is collected in the bottom of chamber 20 in a collection well 48. When the well 48 is filled, overflow is directed back into the bottle 24 through return tube 72.

As discussed hereinabove, one advantage of the present invention over the prior art is the ability of device 10 to entrain atmospheric air, such that the aerosol ultimately delivered to the patient can have a concentration of approximately 28% oxygen. In order to help achieve this beneficial result, the device 10 includes a generally tubular sleeve member 50 circumferentially disposed about the body 10 adjacent the nebulization chamber 16. Sleeve 50 includes an outwardly extending skirt 52 which preferably has ribbing 54 formed on the periphery thereof. Ribbing 54 enables the user to easily grip sleeve 50 and rotate it about the tubular top section 14. It is understood, of course, that other means for gripping sleeve 50 are within the scope of the present invention. To insure that sleeve 50 remains in sliding engagement with the tubular top section 14, an outwardly extending circular ring 51 is formed on section 14 which mates with associated groove 53 formed in the sleeve 50. Of course, other means for joining these two members together are within the scope of the present invention. Downwardly extending annular members 55 formed on the top of sleeve 50 act as bearings against the tubular section 14 so as to further encourage easy rotatability of sleeve 50 about top section 14.

In the preferred embodiment markings 56, shown most clearly in FIG. 1, are disposed about the periphery of skirt 52 and indicate the amount of oxygen which is ultimately being delivered to the patient. A pointer 57 integrally formed on the device 10 enables the user to easily determine and accurately position sleeve 50.

Rotation of sleeve 50 selectively brings into alignment a pair of opposed inlet openings 58 and a pair of opposed generally rectangular inlet ports 60 formed on top of section 14. Inlet openings 58 have an inverted L-shaped configuration which helps encourage air to be drawn into the device 10.

The interaction of the sleeve member 50, inlet ports 60 and the venturi section 22 will now be described. As the pressurized gas flows through gas inlet 62 and is sprayed out through nozzle 34 across nozzle 36, liquid is drawn up through conduit 42. As the liquid is sprayed out through nozzles 36, aerosol spray 41 is created in chamber 16. Aerosol spray 41 is then directed through venturi 22. The effect created by the flow through venturi 22 causes air to be siphoned in through the inlet openings 58 and the inlet port 60 to the extent desired by the user. While some mixing of air and aerosol spray 41 does take place in the nebulization chamber 16, further mixing is achieved in the baffling chamber 20. While a wide variety of various venturi configurations have been used, it has been found that in order to achieve 28% oxygen concentration, a specifically shaped venturi is used. Preferably, venturi section 22 is comprised of a converging wall section 64 and a diverging wall section 68. These two sections form a throat 66 therebetween. Wall section 68 is outwardly inclined at an angle of approximately 5° to 10°. This angle enables venturi 22 to convert the velocity of the aerosol spray 41 flowing therethrough into sufficient head pressure so as to reduce the back pressure developed in the system created during transport of the spray 41 to the patient.

The location of venturi 22 with respect to nozzles 34 and 36 is also important. Preferably venturi 22, and more specifically, section 64, is located downstream of nozzles 34 and 36 so as to permit spray 41 to further increase in velocity as it flows through the other sections of the venturi 22. The placement and configuration of venturi 22 also aids in removing large particles from the aerosol spray 41. More specifically, the aerosol spray 41 is formed at a location such that it impacts upon the section 64. This causes larger particles to collect on venturi 22 thus removing them from spray 41. Furthermore, the configuration of the body 12 provides a straight path for the spray 41 from the top of the nebulization chamber 16, through the venturi 22 and to the baffling chamber 20. It is believed that the use of a straight path, without employing an impaction post, further improves the ability of the device to draw air into the nebulization chamber 16.

Yet another beneficial aspect of the present invention relates to how the nebulizer device 10 is joined to associated bottle 24. In the present invention, a uniquely configured joining assembly 25 is provided on the rectangular bottom section 18. This is best shown with reference to FIGS. 1 and 2. Joining assembly 25 is comprised of the rotatable locking collar 26 as well as first and second puncture probes, 70 and 72, respectively. Puncture probe 70 has a puncturing tip 70a; likewise, puncture probe 72 has a puncture tip 72a as shown in FIGS. 5 and 6. Puncture probes 70 and 72 are integrally formed on a depressed section 76 created on plate member 74. Note that puncture probes 70 and 72 are each provided with openings 71 so as to be in fluid communication with the device 10 as well as the bottle 24. Also extending from member 76 are first and second guides 78 and 78a. Guides 78 and 78a help position and permit ready attachment of the device 10 to bottle 24.

When the device 10 is joined to the associated bottle 24, probes 70 and 72 extend into neck 28. In the preferred embodiment, neck 28 is made of a first neck section 80 and a second neck section 82. Neck section 80 is a conduit integrally formed on bottle 24 which provides a flow path for liquid out of the bottle 24. To insure that all the liquid can be removed, section 80 is joined to the bottle 24 adjacent the bottom thereof. Neck section 82 forms a separate flow path into bottle 24. In this manner, flow into and out of bottle 24 can be readily achieved. Referring to FIG. 2, one can see that probe 70 is inserted directly into section 80 while probe 72 is inserted into section 82. Thus, the need for more complex return fluid systems is obviated.

After insertion of probes 70 and 72, locking collar 26 is rotated about neck 28. Three equally spaced gripping members 27 formed on collar 26 engage three associated shoulders formed on neck 28. The gripping members 27 may be cammed or otherwise shaped to insure a tight seal. Other means for joining device 10 to bottle 24 are also within the scope of this invention. Reservoir 24 is filled with the sterile solution through fill port 84a and sealed with an integral cap portion 84 in such a manner as to maintain sterility of the solution.

A second embodiment for an associated bottle is shown with reference to FIG. 7. As shown in FIG. 7, bottle 86 has a cap 88 which permits entry into bottle 86. Neck 90 has a generally T-shaped configuration 92 which forms three shoulders 94. These shoulders are used to engage the gripping members 27 located on the locking collar 26. In the second embodiment, bottle 86 has an open area 96 formed on the top thereof. A flexible conduit 98 is attached to the first puncture probe 70 and extends to the bottom of bottle 86. Probe 72 is configured and operates as in the first embodiment. It is understood, however, that an alternate configuration for probe 70 and conduit 98 includes an extended puncture probe 70 which would extend down adjacent the bottom of bottle 86. Such construction of bottle 86 enables it to be formed without external conduit 80 as was the case with respect to bottle 24.

Referring again to FIGS. 1 and 2, one can see that an opening 100 is formed in one side wall of section 18. A metal tubular conduit 104 extends into opening 100 and transversely across the chamber 20. Rubber washers 106 are disposed about conduit 104 and are placed in an associated depression 102 formed on each of the side walls. Opening 100 and conduit 104 enable an external heater to be readily joined to the device 10 such that the aerosol 41 is heated in the baffling chamber 20 prior to delivery to the patient. It is understood, that other means for heating the aerosol 41 in the baffling chamber 20 are also within the scope of the present invention. These means include, for example, immersing part or all of the section 18 in a heating medium such as a donut shaped heater, water bath or the like.

In operating the device 10 of the present invention, the device 10 is joined to rectangular bottle 24. Bottle 24 preferably comes prefilled with purified water, saline or like liquids. In this manner, bottle 24 can be stored for a period of time before use. Entry into bottle 24 by the user is achieved by puncturing the bottle 24 in the top of neck 28. To aid in this procedure, the device 10, and more specifically the joining system 25, has guides 78 which engage the neck sections 80 and 82. In this manner puncture probes 70 and 72 are guided toward the top of neck 28. By pressing the device 10 and bottle 24 together, probes 70 and 72 pierce and enter into bottle 24 and plate 74 engages the top of neck 28. Probe 70 is now in flow communication with neck section 80 and probe 72 is in flow communication with neck section 82. Locking collar 26 is now rotated such that gripping members 27 engages associated shoulders formed in the neck 28. Neck 28 and member 27 are configured such that a positive pressure seal is maintained between the interfacing of the bottle 24 and the puncture probes 70, 72. By the use of the joining system 25, a sealed system is achieved which enables the liquid in bottle 24 to flow to an aerosol producing system in body 12. In addition, excess fluid in the body 12 can be returned to the bottle 24 via the probe 72 while the device 10 is operating.

After the device 10 and bottle 24 are secured together, a pressurized oxygen gas source is joined to the device 10 by means of coupling 30. A screw thread may be formed on coupling 30 which mates with a conduit from the gas source. Tubing (not shown) is usually joined to the device 10 at outlet conduit 46. In this manner, the aerosol created in device 10 can be directed to the patient or other end use.

Next, sleeve 50 is rotated by gripping and rotating skirt 52 until the desired amount of oxygen flowing out of the device 10 is indicated by pointer 57 and markings 56. Rotation of sleeve 50 changes the relationship of the inverted L-shaped openings 58 on sleeve 50 with respect to the rectangular inlet ports 60 on the top section 14. When ports 60 are completely closed off by sleeve 50, approximately 100% of the gas leaving the device 10 would be oxygen. Positioning sleeve 50 such that a portion of openings 58 are in flow communication with ports 60 decreases the oxygen concentration of the aerosol flowing to the patient to as low as 28% or even lower.

When pressurized oxygen flows through conduit 32, it is sprayed into the nebulization chamber 16 by nozzle 34. The gas is directed across nozzle 36 and a low pressure zone is created. This causes liquid in bottle 24 to be drawn up through section 80, puncture probe 70, conduit 42 and sprayed into chamber 16. As the liquid enters chamber 16, it is entrained in the gas and carried through the remainder of the device 10 in the form of aerosol spray 41.

The spray 41 flowing through nebulization chamber 16 and venturi 22 causes air to be drawn through openings 58, ports 60 and into the nebulization chamber 16. By providing specifically shaped openings 58, more air is drawn into chamber 16. It is believed that openings 58 create a more efficient channel with less turbulence than would be the case with a generally rectangular opening. Other factors are also believed to aid in causing more air to enter chamber 16. These include placement of nozzle 34 upstream of openings 60, placement of venturi 22 downstream of openings 60, the shape of venturi 22, providing a straight path for the aerosol 41, and the location of venturi 22 with respect to the nozzle 34.

As the spray 41 flows through chamber 16 and into chamber 20, dilution with ambient air takes place. Some dilution may occur in chamber 16 or venturi 22, but to insure complete mixing of the air with the spray 41, baffling chamber 20 is provided. Chamber 20 also acts as a means to remove large particles from the spray 41 as discussed above.

The flow of the spray 41 is then directed out of the baffling chamber 20 by outlet conduit 46. Tubing or other means directs the spray 41 from conduit 46 to the patient or other end use.

Particles of liquid in body 12 which were not carried out of the device 10 in the aerosol spray 41 are collected in chamber 20. Here they initially collect in well 48. Removal of large particles from the spray 41 is aided by the placement of venturi 22 and chamber 20. Placement of venturi 22 downstream of the nozzles 34 and 36, permits sufficient momentum to be achieved by the liquid particles such that when larger particles impinge on the section 64, they are collected and are thus removed from the spray 41. Chamber 20 is located such that some of the spray 41 will impinge on the bottom of chamber 20. This also helps remove larger particles. Further, plate 44 is located in chamber 20 such that a significant portion of spray 41 must flow around plate 44 to reach outlet 46. This too helps remove larger particles from the spray 41.

Metal conduit 104 extends transversely across chamber 20 adjacent the well 48. In this manner, a heater (not shown) can be joined to the device 10 and used to heat the collected water in well 48. Heat transfer through the collected water causes the spray 41 to be heated as it flows through chamber 20.

When well 48 is full, additional liquid is directed along the bottom of chamber 20 to the joining system 25, and more specifically, to probe 72. As the liquid level continues to rise, it would begin to flow through opening 71 in probe 72 back into bottle 24. Thus, the amount of liquid removing in device 10 can be accurately regulated. In the first embodiment of the present invention, bottle 24 is not designed to be refilled. After sufficient liquid is removed from bottle 24 a new, pre-filled bottle would be joined to device 10 in the manner described above. It is understood, however, that bottle 24 can be modified such that a liquid can be added before or during use. This is the case with bottle 86. Bottle 86 obviates the need for the externally formed section 80. Instead, a conduit 98 is joined to probe 70 and extends to the bottom of bottle 86. Other than these differences, operation of device 10 on bottle 86 or 24 would be the same.

A wide variety of other materials, shapes and configurations can be used in this invention and it should therefore be understood that changes can be made without departing from the true spirit or scope of this invention. For example, in the preferred embodiment, the body 12 is preferably made of a polycarbonate resin material but other resins are also within the scope of the present invention. Further, pressurized gases other than oxygen can be used to form spray 41, and atmospheric fluids other than air can be drawn into the device 10. This invention, therefore, is not to be limited to the specific embodiments discussed and illustrated herein.

We claim:

1. A nebulizer device comprising:
(a) a body defining an initial nebulization chamber, a subsequent baffling chamber and a venturi means therebetween;
(b) means on said body for connecting said nebulization chamber to a source of pressurized gas;
(c) air intake means disposed on said body adjacent said nebulization chamber for providing said nebulization chamber with air in predetermined quantities;
(d) aerosol means for producing a conical aerosol spray of fine particles of liquid entrained in said gas and subsequently flowing to said baffling chamber along said flow path, said aerosol means located in said nebulization chamber upstream of said venturi means such that flow of said aerosol through said venturi means draws air through said intake means thereby diluting said aerosol, said nebulization chamber, baffling chamber and venturi means configured so as to form a straight, uninterrupted flow path from said aerosol means to said baffling chamber;
(e) means for supplying said aerosol means with a liquid;
(f) said venturi means located downstream of said air intake means and defined by a converging section in flow communication with said nebulization chamber and a diverging section in flow communication with said baffling chamber, said venturi means increasing the flow rate of air through said intake means and directing said air and said aerosol into said baffling chamber, said aerosol means located in said nebulization chamber sufficiently upstream of said venturi means such that said conical spray impacts on said converging section of said venturi means; and
(g) outlet means in flow communication with said baffling chamber for directing said aerosol out of said baffling chamber.

2. A nebulizer according to claim 1 wherein said intake means comprise a plurality of openings on said body adjacent said nebulization chamber.

3. A nebulizer according to claim 1 including means for regulating the flow of said air through said intake means.

4. A nebulizer according to claim 3 wherein said regulating means comprises a movable member circumferentially disposed about said body adjacent said nebulization chamber, said movable member having shaped orifice means for regulating the flow of said atmospheric fluid through said intake means.

5. A nebulizer according to claim 4 wherein each said orifice means has an inverted generally L-shaped configuration.

6. A nebulizer according to claim 1 wherein said aerosol means includes a first nozzle for directing said gas into said nebulization chamber and a second nozzle for directing said liquid into said nebulization chamber, said second nozzle located downstream from said first nozzle and wherein the discharge end of said second nozzle is inclined upwardly at an angle of about 5° to 20° with respect to vertical such that the higher end of the incline is closer to said first nozzle.

7. A nebulizer according to claim 6 wherein said first nozzle is located upstream of said intake means.

8. A nebulizer according to claim 1 including means for heating said aerosol as it passes through said baffling chamber, said heating means comprising a heat transmitting cylinder transversely mounted in said baffling chamber.

9. A nebulizer according to claim 8 wherein said baffling chamber includes a downwardly extending liquid collection well and said heat transmitting cylinder is disposed adjacent said well.

10. A nebulizer according to claim 1 including a fastener assembly for joining said nebulizer device to an associated bottle, said fastener assembly comprises (i) a locking collar member joined to said body and configured to selectively join said nebulizer device to an associated bottle, containing a liquid, and (ii) first and second puncture probes configured to pierce a selected portion of said bottle, said first puncture probe defining a flow channel for liquid from said bottle to said aerosol means and said second puncture probe defining a flow channel between said baffling chamber and said bottle.

11. A nebulizer according to claim 10 including a bottle containing a liquid joined to said fastener assembly.

12. A nebulizer device comprising:
(a) a body defining an initial nebulization chamber, a subsequent baffling chamber and a venturi means therebetween;
(b) means on said body for connecting said nebulization chamber to a source of pressurized gas;
(c) air intake ports disposed through said body adjacent said nebulization chamber for providing said nebulization chamber with air in predetermined quantities;
(d) a movable sleeve member circumferentially disposed about said body adjacent said nebulization chamber, said sleeve member having shaped openings for regulating the flow of said air through said intake ports;
(e) aerosol means for producing a conical aerosol spray of fine particles of liquid entrained in said gas and subsequently flowing to said baffling chamber along said flow path, said aerosol means located in said nebulization chamber upstream of said venturi means such that flow of said aerosol through said venturi means encourages air to flow through said intake ports thereby diluting said aerosol, said nebulization chamber, baffling chamber and venturi means configured so as to form a straight, uninterrupted flow path from said aerosol means to said baffling chamber;
(f) means for supplying said aerosol means with a liquid;
(g) said venturi means located downstream of said air intake means and defined by a coverging section in flow communication with said nebulization chamber and a diverging section in flow communication with said baffling chamber, said venturi means increasing the flow rate of said air through said intake means and directing said air and said aerosol into said baffling chamber, said aerosol means located in said nebulization chamber sufficiently upstream of said venturi means such that said conical spray impacts on said converging section of said venturi means;
(h) outlet means in flow communication with said baffling chamber for directing said aerosol out of said baffling chamber; and
(i) means for joining said nebulizer device to an associated bottle, said joining means having first and second puncture probes extending into said baffling chamber and configured to pierce a selected portion of said bottle, said first puncture probe defining a flow channel for liquid from said bottle to said aerosol means and said second puncture probe defining a flow channel between said baffling chamber and said bottle.

13. A nebulizer according to claim 12 wherein said openings on said sleeve member have an inverted generally L-shaped configuration.

14. A nebulizer according to claim 12 wherein said aerosol means includes a first nozzle for directing said gas into said nebulization chamber and a second nozzle for directing said liquid into said nebulization chamber, said second nozzle located downstream from said first nozzle and wherein the discharge end of said second nozzle is inclined upwardly at an angle of about 5° to 20° with respect to vertical such that the higher end of the incline is closer to said first nozzle.

15. A nebulizer according to claim 12 wherein said joining means includes a rotatable locking collar joined to said body and configured to selectively join said nebulizer device to an associated bottle.

16. A nebulizer according to claim 15 wherein said first puncture probe directs liquid in said bottle to said aerosol means and said second puncture probe directs liquid collected in said baffling chamber back to said bottle.

17. A nebulizer according to claim 15 wherein said locking collar includes a plurality of gripping members configured to selectively engage on said bottle.

18. A nebulizer according to claim 17 including a bottle joined to said nebulizer device, said bottle having a first conduit in flow communication with said bottle adjacent the bottom thereof and a second conduit in flow communication with said bottle adjacent the top thereof.

19. A nebulizer according to claim 18 wherein said bottle include a plurality of members which are engaged by said joining means.

20. A nebulizer according to claim 18 wherein said first and second conduits form a neck on said bottle with said first conduit joined to said first probe and said second conduit joined to said second probe.

21. A nebulizer according to claim 12 including a bottle having neck with a generally T-shaped cross-section, said nebulizer device joined to said bottle adjacent said neck such that said first and second probes enter into said bottle.

22. A nebulizer according to claim 21 wherein a conduit extends from said first probe to a point adjacent the bottom of said bottle.

* * * * *